United States Patent [19]

Benson et al.

[11] 4,054,651

[45] Oct. 18, 1977

[54] METHOD OF CONTRACEPTION

[75] Inventors: Harvey D. Benson, Cincinnati; Joyce Francis Grunwell, Hamilton; John O'Neal Johnston, Cincinnati, all of Ohio; Vladimir Petrow, Chapel Hill, N.C.

[73] Assignee: Richardson-Merrell Inc., Wilton, Conn.

[21] Appl. No.: 684,943

[22] Filed: May 10, 1976

[51] Int. Cl.$^2$ .................... C07J 1/00; A61K 31/56
[52] U.S. Cl. ............................. 424/239; 260/397.4
[58] Field of Search .................. 424/239, 242, 243

[56] References Cited

U.S. PATENT DOCUMENTS 3,449,381  6/1969  Bowers .......................... 260/397.4

Primary Examiner—Elbert L. Roberts
Attorney, Agent, or Firm—L. Ruth Hattan; Eugene O. Retter; George W. Rauchfuss, Jr.

[57] ABSTRACT

A method of contraception which comprises administering a compound of the following general formula:

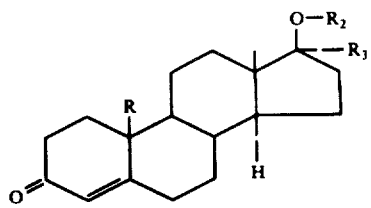

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17-position carbon atom and the oxygen atom either alone or in combination with a progestogen.

28 Claims, No Drawings

METHOD OF CONTRACEPTION

FIELD OF INVENTION

This invention relates to methods of contraception and pharmaceutical compositions useful for the same.

BACKGROUND OF INVENTION

It is known to those skilled in the art that progestogenic steroids, either singly or in combination, may be used to control the fertility of warm blooded animals. Various products and three primary regimens are presently in use and in particular the following:

Combination regimens containing an estrogen and a progestogen which are generally administered from day five of a menstrual cycle for 20 or 21 days;

Sequential/serial regimens in which an estrogen is administered generally from day five of the cycle followed sequentially by an estrogen-progestogen combination, various regimens of which have been proposed; and continuous progestogen regimen (or mini-pill) in which a progestogen is administered daily.

Combination regimen and sequential/serial regimen inhibit ovulation with great efficiency. Continuous progestogen regimen utilizes a dose of steroidal progestogen so small that it does not induce ovulation inhibition in the majority of users who continue to ovulate and to cycle essentially as they would without progestogen. However, as is well known to those skilled in the art, use of this regimen is accompanied by a sufficiently high incidence of uterine spotting and extended bleeding to markedly reduce the utility and attractiveness of the method for contraception and as an instrument for population control. Various proposals have been made for reducing the incidence of spotting and extended bleeding, for example, the addition of estrogen to the progestogen for the last few days of each cycle.

Although estrogens have proven to provide an effective means of contraception it is known that certain undesirable side effects may result from their use. Ethinyl estradiol and mestranol, which represent estrogenic components in current oral contraceptives, are known to be involved in certain serious side effects associated with oral contraceptives including depression (Nature 243, 58 (1973)), hypertension (Am. J. Obstet. Gynecol. 112, 912 (1972)), carbohydrate and lipid abnormalities (Lancet 1969, October 11, 783), interference with blood clotting mechanisms resulting in thrombosis and stroke (Ann. Intern Med. 72, 111 (1970)), and jaundice (Am. J. Obstet. Gynecol. 119, 165 (1974)). Consequently, there is a need for an improved method of contraception.

The present invention provides a novel method of contraception which avoids many of the undesirable side effects which may occur with the use of estrogens as will become more apparent hereinafter.

Some of the compounds employed in the instant invention, for example, 19-hydroxyandrost-4-ene-3,17-dione and the 19-oxo derivative thereof have been involved in numerous in vitro studies wherein the role in the metabolism of androgen has been investigated. Additionally, 19-hydroxy- androst-4-ene-3,17-dione is reported to have been administered to two healthy male subjects each 21 years of age (J. Clin. Endocrinol. Metab. 28, 1401 (1968)). Also, 3-oxo-17β-hydroxyandrost-4-en-19-al has been reported in U.S. Pat. No. 3,235,573 issued Feb. 15, 1966, and U.S. Pat. No. 3,449,381 issued June 10. 1969 wherein the utilities disclosed are anabolic-androgenic activity, inhibition of pituitary gonadotrophins and adrenocorticotrophin, antiestrogenic, blood, liver and adrenal cholesterol lowering properties, control of fertility and psychotic conditions, and appetite stimulants. To applicant's knowledge the use of the compounds employed in the present invention as contraceptive agents by the inhibition of ovulation has not been taught or suggested heretofore.

SUMMARY OF INVENTION

This invention relates to a method of contraception which comprises administering alone or in combination with a progestogen a compound of the following formula and to pharmaceutical compositions useful as contraceptives.

Formula I

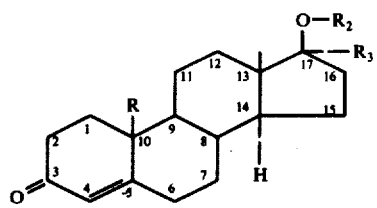

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17- position carbon atom and the oxygen atom.

DETAILED DESCRIPTION OF INVENTION

In the compounds of general Formula I the term alkylcarbonyl is taken to mean a group of the structure

wherein the alkyl moiety has from 1 to 20 carbon atoms and can be a straight chain or a branched chain. Illustrative examples of the alkyl moiety in the substituent alkylcarbonyl group are methyl, ethyl, n-propyl, isopropyl, n-butyl, sec-butyl, tert-butyl, n-pentyl, neopentyl, pivalyl, hexyl, heptyl, octyl, 2,4-dimethyloctyl, undecyl, 9-methylundecyl, pentadecyl, hexadecyl, dodecyl, 2,4,6-trimethyldecyl, heptadecyl, decyl, octadecyl, nonadecyl and didecyl.

The term benzoyl as used in reference to the compounds of general Formula I is taken to mean the group

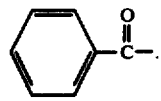

The term phenylalkylcarbonyl as used in reference to the compounds of general Formula I is taken to mean a substituent group of the structure

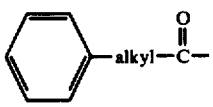

wherein the alkyl moiety, which may also be referred to as an alkylene moiety, has from 1 to 6 carbon atoms and can be a straight chain or a branched chain. Illustrative examples of the alkyl moiety in the substituent phenylalkylcarbonyl group are methyl, ethyl, n-propyl, n-butyl, n-pentyl, hexyl, isopropyl, sec-butyl, tert-butyl and neopentyl.

Illustrative examples of cycloalkylcarbonyl groups which $R_1$ and $R_2$ may be are cyclopentanecarbonyl, cyclohexanecarbonyl, cyclooctanecarbonyl, 1- or 2-norbornanecarbonyl and 1- or 2-adamantanecarbonyl.

It is apparent from the foregoing general Formula I that the compounds employed in the instant invention are androst-4-ene-3,17-diones having a —CH$_2$OR$_1$ or —CHO group at the 10β-position as represented respectively by the following general Formulas II and III, or are 17β-hydroxyandrost-4-en-3-one derivatives or esters thereof as defined by $R_2$ having a —CH$_2$OR$_1$ or —CHO group present at the 10β-position as repesented respectively by the following general Formulas IV and V:

Formula II

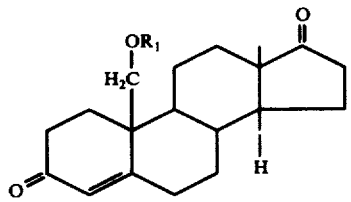

Formula III

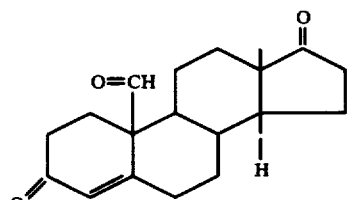

Formula IV

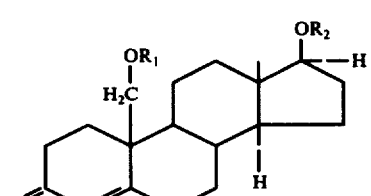

Formula V

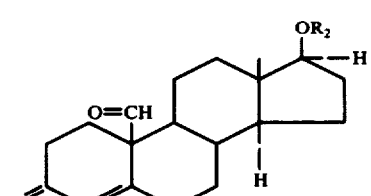

In general Formulas II and IV $R_1$ is hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms as defined hereinabove.

In general Formulas IV and V the hydrogen atom attached to the 17- position is in the alpha position, and $R_2$ is hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or, cycloalkylcarbonyl wherein the cycloalkyl moiety has from 5 to 10 carbon atoms as defined hereinabove.

In practicing the present invention the compounds of general Formula I are used alone or in combination with progestogens. Illustrative progestogens which may be used in practicing the present invention for oral or parenteral use are the following:

| | |
|---|---|
| norethindrone | 17-hydroxy-19-nor-17α-pregn-4-en-20-yn-3-one |
| norethindrone acetate | 17-hydroxy-19-nor-17α-pregn-4-en-20-yn-3-one acetate |
| norethynodrel | 17-hydroxy-19-nor-17α-pregn-5(10)-en-20-yn-3-one |
| lynestrenol | 17-hydroxy-19-nor-17α-pregn-4-en-20-yn |
| ethynodiol diacetate | 19-nor-17α-pregn-4-en-20-yne-3β,17-diol diacetate |
| quingestanol | 3-cyclopentyloxy-19-nor-17α-pregna-3,5-diene-20-yn-17-ol acetate |
| algestone acetophenide | 16α(R), 17-[(1-phenylethylidene)bis(oxy)]-pregn-4-ene-3,20-dione |
| medroxyprogesterone acetate | 17-hydroxy-6α-methyl-pregn-4-ene-3,20-dione acetate |
| megestrol acetate | 17α-hydroxy-6-methyl-pregna-4,6-diene-3,20-dione acetate |
| melengestrol acetate | 17α-hydroxy-6-methyl-16-methylene-4,6-diene-3,20-dione acetate |
| dimethisterone | 17β-hydroxy-6α-methyl-17-(1-propynyl)androst-4-en-3-one monohydrate |
| norgestrel | 13-ethyl-17-hydroxy-18,19-dinor-17α-pregn-4-en-20-yn-3-one |

The compounds of general Formula I are useful as contraceptive agents in that said compounds prevent ovulation, that is, the compounds of general Formula I are ovulation inhibitors. When the compounds of general Formula I are used in combination with a progestogen, the compounds of general Formula I are effective as ovulation inhibitors, and the progestogen is used to induce a cyclic bleeding resembling a cyclic menses bleeding and also synergize the effect of the compounds of general Formula I. In practicing the present invention the compounds of general Formula I either alone or in combination with a progestogen can be administered for purposes of contraception either alone or in the form of a pharmaceutical formulation to a patient which term is taken to mean fertile female mammals, for example, human fertile females, fertile ewes, bovine cows, sows, mares, female dogs, cats, mice and rats.

The amount of each type of compound, that is, the compounds of general Formula I and the progestogen administered varies. When used alone or in combination with a progestogen the amount of compound of general Formula I that is administered is any contraceptive effective amount or any ovulation inhibitory effective amount of from 0.01 up to 3.0 mg/kg and preferably from 0.1 to 1.0 mg/kg. For parenteral administration, that is, subcutaneous or intramuscular administration, it is preferred that the amount of compound of general Formula I administered be from 0.01 up to 1.0 mg/kg and within this range preferably from 0.1 to 0.5 mg/kg. When a progestogen is employed in practicing the present invention the amount administered is any nonovulation inhibiting amount of from 0.005 to 0.5 mg/kg. Unit dosages of the compounds of general Formula I may be, for example, 50 mg to 150 mg and of the progestogen may be, for example, 1.5 mg to 25 mg. The amount of compound of general Formula I employed will vary with the mode of administration it being known that in the area of contraception lower doses per day are required for administration via implant, polymeric inserts, or intrauterine device than are required, for example, for oral administration. An implant or insert is used only when the androstenes, that is the compounds of general Formula I are used alone.

The compounds employed in the present invention may be administered by different regimens. When the compounds of general Formula I are used alone said compounds can be administered continuously on from day 5 to day 21 of the cycle. When a progestogen is employed in the present invention the progestogen and the compounds of general Formula I can be administered together continuously on from day 5 to day 21 of the cycle, or the compounds of general Formula I can be administered on from day 5 to day 21 and the progestogen administered on from day 16 to day 21 of the cycle.

A preferred embodiment of the present invention is the use as contraceptive agents of the compounds of general Formulas II and III with the use of the compounds of general Formula III representing a more preferred embodiment. Other embodiments of this invention are the use as contraceptive agents of the compounds of general Formulas IV and V with the use of the compounds of general Formula IV wherein $R_1$ and $R_2$ each represent hydrogen and the compounds of general Formula V wherein $R_2$ represents hydrogen being more preferred embodiments. When a progestogen is employed in the present invention preferred progestogens are norethindrone acetate, lynestrenol, ethynodiol diacetate and norgestrel.

For oral administration the compounds can be formulated into solid or liquid preparations such as capsules, pills, tablets, troches, powders, solutions, suspensions or emulsions. The compounds can be applied in the form of an aerosol containing finely divided particles of the active ingredient or a solution, suspension or emulsion of the active ingredient. The solid unit dosage forms can be a capsule which can be of the ordinary gelatin type containing a compound of general Formula I and a carrier, for example, lubricants and inert filler such as lactose, sucrose, and cornstarch. In another embodiment the compounds of general Formula I can be tableted with conventional tablet bases such as lactose, sucrose and corn starch in combination with binders such as acacia, corn starch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

Following are illustrative pharmaceutical formulations which may be employed in practicing the present invention:

| Aerosol Foam | |
|---|---|
| 3,17-Dioxoandrost-4-en-19-al | 1.0 g |
| Propylene Glycol | 96.0 g |
| Emulsifying Wax NF XIV | 3.0 g |
| Dichlorodifluoromethane:cryofluorane (20:80) | 6.9 g |

Dissolve the drug substance in the propylene glycol. Add the emulsifying wax and heat to approximately 70° C. Stir while cooling to room temperature. Charge a suitable aerosol unit with this concentrate and 6.9 g of dichlorodifluoromethane: cryofluorane (20:80).

| Tablet | For 15,000 |
|---|---|
| 3,17-Dioxoandrost-4-en-19-al Fine Powder | 75 g |
| Lactose | 1.216 Kg |
| Corn Starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| Magnesium Stearate | 0.015 Kg |
|---|---|
| Corn Starch qs ad | 1.725 Kg |

Compress on a suitable tablet machine to a weight of 0.115 g/tablet.

| Soft Gelatin Capsule | |
|---|---|
| 3,17-Dioxoandrost-4-en-19-al | 0.25 Kg |
| Polysorbate 80 | 0.25 Kg |
| Corn Oil qs ad | 25.0 Kg |

Mix and fill into 50,000 soft gelatin capsules.

| IM Depot Injection | |
|---|---|
| Each 1 ml contains the following: | |
| 3,17-Dioxoandrost-4-en-19-al | 5.0 mg |
| Anhydrous Chlorobutanol | 5.0 mg |
| Aluminum Monostearate | 50.0 mg |
| Peanut Oil qs ad | 1.0 ml |

Dissolve or disperse the ingredients in the peanut oil.

| Depot - Implant | |
|---|---|
| 3,17-Dioxoandrost-4-en-19-al micronized | 5 mg |
| Dimethylsiloxane | 240 mg |
| Catalyst qs | |

Disperse the drug substance in the fluid dimethylsiloxane. Add the catalyst and cast into a suitable monolytic structure.

Alternatively, the drug substance may be enclosed by a precast polydimethylsiloxane envelope.

Alternatively, the drug substance may be dispersed in a suitable amount of hydroxyethyl acrylate subsequently polymerized and cross-linked by the addition of ethylenedimethacrylate, and an oxidizing agent, to yield a 3-dimensional ethylene glycomethacrylate mouldable gel (Hydron).

| IM Injections | | |
|---|---|---|
| A. | Oil Type: | |
| | 3,17-Dioxoandrost-4-en-19-al | 25 mg |
| | BHA, BHT aa | 0.01% w/v |
| | Peanut Oil or Sesame Oil qs | 1.0 ml |
| B. | Suspension Type: | |
| | 3,17-Dioxoandrost-4-en-19-al micronized | 25 mg |
| | Sodium Carboxymethylcellulose | 0.5 w/v |
| | Sodium Bisulfite | 0.02% w/v |

| Aerosol Foam | |
|---|---|
| 3,17-Dioxoandrost-4-en-19-al | 1.0 g |
| Norethindrone | 0.05 g |
| Propylene glycol | 96 g |
| Emulsifying Wax NF XIV | 3.0 g |
| Dichlorodifluoromethane:Cryofluorane (20:80) | 6.9 g |

Dissolve the drug substance in the propylene glycol. Add the emulsifying wax and heat to approximately 70° C. Stir while cooling to room temperature. Charge a suitable aerosol unit with this concentrate and 6.9 g of dichlorofluoromethane:cryofluorane (20:80).

| IM Depot Injection | |
|---|---|
| Each 1 ml contains the following: | |
| 3,17-Dioxoandrost-4-en-19-al | 5.0 mg |
| Norethindrone | 0.05 mg |
| Anhydrous chlorobutanol | 5.0 mg |
| Aluminum monostearate | 50.0 mg |
| Peanut oil qs ad | 1.0 ml |

Dissolve or disperse the ingredients in the peanut oil.

The following tabulation describes illustrative tablet formulations containing as active ingredients a progestogen and compounds of general Formula I, the latter represented as compound 1 or compound 2 each defined following the tabulation. To prepare these representative tablet formulations the active ingredients are combined with the filler and internal disintegrant and thoroughly mixed. The binder is granulated and passed through a No. 6 mesh screen and dried to a moisture content of approximately 2.5%. The dry granules are screened through a No. 12 mesh screen after which the lubricant and external disintegrant are added and thoroughly mixed. The tablets are compressed on a suitable tablet machine to a weight of 0.250 g/tablet.

| | For The Manufacture of 15,000 Tablets at 250 mg/Tablet | | | | | | |
|---|---|---|---|---|---|---|---|
| Progestion/ Estrogen Combination | mg/ Tablet | kg/ Batch | Filler Lactose, kg | Internal Disintegrant Corn Starch, kg | Binder 10% Starch Paste, kg | Lubricant Magnesium Stearate, kg | External Disintegrant Corn Starch, kg |
| Megestrol Acetate | 4 | 0.06 | 1.248 | 0.65 | qs | 0.0375 | qs ad 3.75 |
| Compound 1 | 100 | 1.5 | | | | | |
| Megestrol Acetate | 4 | 0.06 | 1.878 | 0.65 | qs | 0.0375 | qs ad 3.75 |
| Compound 2 | 50 | 0.75 | | | | | |
| Norethindrone | 1 | 0.015 | 2.372 | 0.65 | qs | 0.0375 | qs ad 3.75 |
| Compound 1 | 20 | 0.3 | | | | | |
| Norethindrone | 1 | 0.015 | 2.520 | 0.65 | qs | 0.0375 | qs ad 3.75 |
| Compound 2 | 10 | 0.15 | | | | | |
| Norethindrone | 1.5 | 0.0225 | 2.215 | 0.65 | qs | 0.0375 | qs ad 3.75 |
| Compound 1 | 30 | 0.45 | | | | | |
| Norethindrone | 1.5 | 0.0225 | 2.440 | 0.65 | qs | 0.0375 | qs ad 3.75 |
| Compound 2 | 15 | 0.225 | | | | | |
| Ethynodiol diacetate | 1 | 0.015 | 1.923 | 0.65 | qs | 0.0375 | qs ad 3.75 |
| Compound 1 | 50 | 0.75 | | | | | |
| Ethynodiol diacetate | 1 | 0.375 | 2.280 | 0.65 | qs | 0.0375 | qs ad 3.75 |
| Compound 2 | 25 | 0.375 | | | | | |
| Norgestrel | 0.5 | 0.0075 | 1.930 | 0.65 | qs | 0.0375 | qs ad 3.75 |
| Compound 1 | 50 | 0.75 | | | | | |
| Norgestrel | 0.5 | 0.0075 | 2.305 | 0.65 | qs | 0.0375 | qs ad 3.75 |
| Compound 2 | 25 | 0.375 | | | | | |
| Norethynodrel | 5 | 0.075 | 2.163 | 0.65 | qs | 0.0375 | qs ad 3.75 |
| Compound 1 | 30 | 0.45 | | | | | |
| Norethynodrel | 5 | 0.075 | 2.388 | 0.65 | qs | 0.0375 | aw ad 3.75 |
| Compound 2 | 15 | 0.225 | | | | | |
| Dimethisterone | 25 | 0.375 | 0.813 | 0.65 | qs | 0.0375 | qs ad 3.75 |
| Compound 1 | 100 | 1.5 | | | | | |
| Dimethisterone | 25 | 0.375 | 1.563 | 0.65 | qs | 0.0375 | qs ad 3.75 |
| Compound 2 | 50 | 0.75 | | | | | |

Compound 1 = 3,17-Dioxoandrost-4-en-19-al
Compound 2 = 3-Oxo-17β-hydroxyandrost-4-en-19-al

| Water for injection, qs | 1.0 ml |
|---|---|

Administration of the compounds of general Formulas I to V to a patient in need thereof in the effective amounts described hereinabove achieves the desired contraceptive or anti-ovulatory effect without the occurrence of certain deleterious side effects reported to occur with the administration of estrogenic agents including uterine growth and thrombotic effects, such as, blood clotting. Administration of the compounds employed in the present invention in amounts higher than that specified above as an effective amount may result in these deleterious estrogenic side effects.

To demonstrate the ovulation inhibitory effect of the compounds of general Formula I immature female Sprague-Dawley rats were treated daily on the 19th through the 24th day of age with various dosage concentrations of a compound of general Formula I. On the twenty-second day of age each rat was injected with two international units of a gonadotrophin, for example, pregnant mare's serum to induce ovulation. The number of ova present in the ovaduct was determined on the morning of the twenty-fifth day. The followihng tabulation shows the effect of 3,17-dioxoandrost-4-en-19-al in this test system.

| Treatment | Ovulation-Inhibition | | | |
|---|---|---|---|---|
| | Dose (mg/day) | No. Rats | % Ovulating | Total No. Ova |
| Vehicle | — | 6 | 83 | 28 |
| 3,17-Dioxoandrost-4-en-19-al | 1.0 | 6 | 33 | 6* |

*Significantly different from vehicle treated control, P< 0.05

The data contained in the following tabulation indicate that 3,17-dioxoandrost-4-en-19-al does not bind in vitro with the estrogen receptor of uterine estrogen target tissue. This binding is the first step necessary for hormonal action. To obtain these data female hamsters were ovariectomized and uterine cytosol was prepared 24 to 48 hours post surgery. Concentrations of $4 \times 10^{-6}$ to $4 \times 10^{-10}$ molar were compared for competitive bindings of $H^3$-estradiol-17$\beta$-labeled cytosol receptor sites according to the methods of Leavitt et al., Endocrin. 94, 1041 (1974) and Korenman, J. Clin. Endocrin. and Metab. 28, 127 (1968). The relative binding was compared with estradiol which was equated to 100.

| Treatment | Uterine Cytosol Affinity |
|---|---|
| | Relative Estrogen Binding Affinity |
| Estradiol | 100 |
| Estrone | 22 |
| Estriol | 10 |
| 3,17-Dioxoandrost-4-en-19-al | 0.01 |

The lack of estrogen binding affinity of 3,17-dioxoandrost-4-en-19-al supports the finding of lack of certain estrogenic side effects of the compounds employed in the present invention.

It has also been found that the compounds employed in the present invention have no thrombotic potential. For example, 3,17dioxoandrost-4-en-19-al was given subcutaneously to ovariectomized albino rats for 7 days at either 0.1 or 3.0 mg/kg. Body weight and uterine weights were measured. Blood samples were taken and the effect on thrombotic potential determined through measurements of anti-thrombin III activity, ethanol get tests, (fibrin monomer level), protamine sulfate test (fibrin degradation products), adenosinediphosphate and collagen induced platelet aggregation. Anti-thrombin activity was not affected nor was increased fibrin monomer or fibrin degradation product level detected. Platelet aggregation was not significantly changed.

Dydrogesterone is another example of a progestogen which may be employed in the present invention and chemically is 9$\beta$, 10$\alpha$-pregna-4,6-diene-3,20-dione.

Many of the compounds employed in the present invention are known in the art or are commercially available. For example, 19-hydroxyandrost-4-ene-3,17-dione, 17$\beta$, 19- dihydroxyandrost-4-en-3-one, 19-hydroxy-17$\beta$-(1-oxoethoxy)- androst-4-en-3-one, 19-hydroxy-17$\beta$-(1-oxobenzyloxy)androst- 4-en-3-one and 3-oxo-17$\beta$(1-oxobenxyloxy)androst-4-en-19-al are commercially available.

The esters of the compounds employed in the present invention, that is, compounds wherein either or both of $R_1$ and $R_2$ are alkylcarbonyl wherein the alkyl moiety has from 1 to 20 carbon atoms and is straight or branched, cycloalkylcarbonyl wherein the cycloalkyl moiety has from 5 to 10 carbon atoms, benzoyl and phenylalkylcarbonyl wherein the alkyl moiety has from 1 to 6 carbon atoms and is straight or branched can be prepared as follows although other methods may also be employed. Ester derivatives of 19-hydroxyandrost-4-ene-3,17-dione and bis-ester derivatives of 17$\beta$,19-dihydroxyandrost-4-en-3-one are prepared by reacting the corresponding 19-hydroxy or 17$\beta$,19-dihydroxy compound with an appropriate acid anhydride of the formula

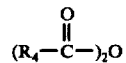

or acid chloride of the formula

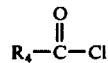

wherein $R_4$ is an alkyl group of from 1 to 20 carbon atoms and is straight or branched, a cycloalkyl group of from 5 to 10 carbon atoms, phenyl or phenylalkyl wherein the alkyl moiety has from 1 to 60 carbon atoms and is straight or branched in the presence of a base such as pyridine, quinoline or trialkylamine, such as, triethylamine, which base serves as the solvent, for from 1 to 24 hours at a temperature of from about 25° to 100° C. The appropriate acid anhydride or acid chloride are known in the art or can be prepared from the corresponding acids by procedures well known in the art.

Compounds employed in the present invention wherein $R_1$ is hydrogen and $R_2$ forms an ester group are prepared from the above obtained 17$\beta$,19-diester derivatives by refluxing the diester with one equivalent of sodium carbonate or potassium bicarbonate or one-half equivalent of sodium carbonate or potassium carbonate or dilute sodium hydroxide or potassium hydroxide solution in a lower alcohol solvent such as methanol or ethanol and water for about one hour, the reflux temperature depending on the solvent system employed.

Compounds employed in the present invention wherein R is CHO and $R_2$ forms an ester group are prepared by dissolving the above obtained compounds wherein $R_1$ is hydrogen and $R_2$ forms an ester group in acetone cooled to 0° to 10° C and treating the solution with sufficient Jones reagent to effect the oxidation. Jones reagent is prepared by standard procedures using 26.72 grams of chromium trioxide, 23 ml of concentrated sulfuric acid and water to make 100 ml. The Jones reagent can be added to the solution until the reddish brown color persists which requires about 289 ml. Other oxidizing agents can be used, such as, dicyclohexylcarbodiimide in dimethylsulfoxide.

The following specific examples further illustrate the preparation of compounds employed in the instant invention.

EXAMPLE 1

17β,19-Bis(1-oxopropoxy)androst-4-en-3-one

A solution of 10 g of 17β,19-dihydroxyandrost-4-en-3-one which is commercially available and 25 ml of propionic anhydride in 200 ml of pyridine is allowed to stand overnight after which 100 ml of ethanol is added, and the reaction mixture is stirred for one hour. The mixture is then poured into one liter of water and the solid product is collected by filtration. The solid is dissolved in ether, dried over magnesium sulfate, filtered and the solvent removed. The residue is dissolved in hot hexane and allowed to cool yielding 17β,19-bis(1-oxopropoxy)androst-4-en-3-one. M.P. 82°–84° C.

EXAMPLE 2

17β,19-Dihydroxyandrost-4-en-3-one

A solution of 150 g of 19-hydroxyandrost-4-en-3-one in 6 liters of ethanol is cooled in an ice bath. To this cold solution is added 13.5 g of potassium borohydride, and the reaction mixture is stirred for 2 hours at about 0° C after which a second 13.5 g or potassium borohydride is added. Two hours later a third 13.5 g portion of potassium borohydride is added to the reaction mixture which is stirred for an additional 1 hour then poured into 11 liters of water to which 70 ml of acetic acid is added. The ethanol is distilled off under reduced pressure and the aqueous residue cooled to 0° C. The solid which separates is filtered off, dried and dissolved in 25 liters of hot chloroform after which the temperature is adjusted to 25° C. To the chloroform solution is added 250 g of manganese dioxide, and the mixture is stirred for 2 hours then filtered and the solvents removed under reduced pressure. The solid residue is recrystallized from acetonitrile to give 17β,19-dihydroxyandrost-4-en-3-one. M.P. 205°–207° C.

EXAMPLE 3

19Hydroxy-17β(1-oxopropoxy)androst-4-en-3-one

A solution of 11 g of 17β,19-bis(1-oxopropoxy)androst-4-en-3-one in 2 liters of methanol is treated with 2.5 g of sodium carbonate in 250 ml of water and refluxed for one hour after which the reaction mixture is poured into 10 liters of water, and the solid collected by filtration. The solid is dissolved in methylene chloride, dried over magnesium sulfate, filtered and the solvent removed. The residue is crystallized from acetone-hexane yielding 6 g of 19-hydroxy-17β(1-oxopropoxy)androst-4-en-3-one. M.P. 160°–162° C.

EXAMPLE 4

19-Acetoxyandrost-4-ene-3,17-dione

A solution of 19-hydroxyandrost-4-ene-3,17-dione in acetic anhydride and pyridine is allowed to stand overnight after which the reaction mixture is poured into ice water. The resulting solid is collected, dried and recrystallized from hexane to give 19-acetoxyandrost-4-ene-3,17-dione.

EXAMPLE 5

19-Acetoxy-17β-hydroxyandrost-4-en-3-one

To a solution of 25.6 g of 19-acetoxyandrost-4-ene-3,17-dione in 4 liters of methanol cooled to 0° C is added 3.1 g of sodium borohydride, and the mixture is stirred at 0° C for 1 hour after which 30 ml of acetic acid is added and the methanol removed under reduced pressure. The resulting residue is taken up in ethyl acetate and washed with water. The organic layer is dried over magnesium sulfate, filtered and the solvent removed. The solid residue is dissolved in 2 liters of chloroform treated with 125 g of manganese dioxide and stirred for 2 hours. The reaction mixture is filtered, and the solvent removed under reduced pressure. The residue is chromatagraphed on alumina using benzene-ether (1:1) as the eluant. The product is recrystallized from acetone-hexane to give 19-acetoxy-17β-hydroxyandrost-4-en-3-one, M.P. 125°–127° C.

EXAMPLE 6

19-Hydroxy-17β(2'-tetrahydropyranylozxy)androst-4-en-3-one

To a solution of 10 g of 19-acetoxy-17β-hydroxyandrost- 4en-3-one in 300 ml of dihydropyran is added a small crystal of p-toluene sulfonic acid. The reaction mixture is allowed to stand overnight after which it is dissolved in ether and extracted with dilute sodium bicarbonate. The ether layer is dried over magnesium sulfate, filtered and the solvent removed. The resulting residue is dissolved in 2 liters of methanol and 2.5 g of sodium bicarbonate in 250 ml of water is added. The methanol solution is refluxed for one hour after which the solvent is removed under reduced pressure at 40° C. The residue is covered with water, and the solid crude product collected and recrystallized from ethylacetate yielding 19-hydroxy-17β(2'-tetrahydropyranyloxy)androst-4-en-3-one. M.P. 193°–199° C.

EXAMPLE 7

3-Oxo-17β-hydroxyandrost-4-en-19-al

A solution of 7 g of 19-hydroxy-17β-(2'tetrahydropyranyloxy)androst-4-en-3-one in 500 ml of acetone is cooled to 10° C and 5.3 ml of Jones reagent is added dropwise. The reaction is stirred for an additional 10 minutes then poured into water and extracted with ethylacetate. The ethylacetate extract is dried over magnesium sulfate, filtered and the solvent removed under reduced pressure. The residue is dissolved in 250 ml of 95% ethanol and 2 ml of concentrated hydrochloridic acid is added. The ethanol solution is refluxed for one hour then cooled to room temperature and neutralized with solid sodium carbonate. The neutralized solution is diluted with water and extracted with ethyl acetate. The extract is dried over magnesium sulfate, filtered and the solvent removed leaving a residue which is chromatagraphed on alumina using 25% ether in benzene as the eluant to give the product 3-oxo-17β-hydroxyandrost-4-en-19-al, M.P. 125°–127° C.

EXAMPLE 8

19-(1-Adamantanylcarbonyloxy)androst-4-ene-3,17-dione

A solution of 22 g of 19-hydroxyandrost-4-ene-3,17-dione, 18 g of 1-adamantanecarboxylic acid chloride, and 29 ml of pyridine in 2.2 liters of toluene is refluxed overnight. The reaction mixture is cooled, and the toluene layer is washed with water, dried over magnesium sulfate and filtered then the solvent is removed. The resulting residue is crystallized from methanol to give 19-(1-adamantanylcarbonyloxy)androst-4-ene-3,17-dione, M.P. 161°–163° C.

EXAMPLE 9

3,17-Dioxoandrost-4-en-19-al

To a solution of 30 g. of 19-hydroxyandrost-4-ene-3,17-dione in 3 liters of acetone cooled in an ice bath is added 28 ml of Jones reagent over a one hour period. The reaction mixture is stirred for an additional fifteen minutes, filtered and the solvent removed under reduced pressure at 35° C. The residue is taken up in a large volume of ether and 1.5 liters of water. The ether layer is collected, dried over magnesium sulfate, filtered and the solvent removed. The residue is crystallized from acetone-hexane to give 3,17-dioxoandrost-4-en-19-al, M.P. 126°-129° C.

EXAMPLE 10

3-Oxo-17β-(1-oxopropoxy)androst-4-en-19-al

To a solution of 14 g of 19-hydroxy-17β-(1-oxopropoxy) androst-4-en-3-one in 1 liter of acetone cooled in an ice bath is added 13.3 ml of Jones reagent over one hour after which the reaction mixture is poured into a large volume of water and extracted with ether. The ether extract is dried over magnesium sulfate, filtered and the solvent removed. The residue is crystallized from acetone-hexane to give 3-oxo-17β(1oxopropoxy)androst-4en-19-al, M.P. 119°-121° C.

We claim

1. A method of contraception in a patient in need thereof which comprises administering to said patient a contraceptive effective amount of a compound of the formula:

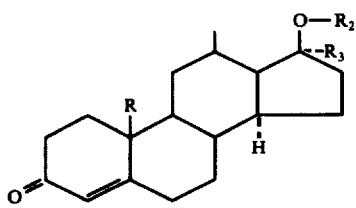

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17- position carbon atom and the oxygen atom.

2. The method of claim 1 wherein the compound is administered continuously on from day five to day twenty-one of the cycle.

3. The method of claim 2 wherein the compound is administered orally in an amount of from 0.01 up to 3.0 mg/kg.

4. The method of claim 2 wherein the compound is administered orally in an amount of from 0.1 to 1.0 mg/kg.

5. The method of claim 2 wherein the compound is administered parenterally in an amount of from 0.01 up to 1.0 mg/kg.

6. The method of claim 2 wherein the compound is administered parenterally in an amount of from 0.1 to 0.5 mg/kg.

7. The method of claim 2 wherein R is —CHO.

8. The method of claim 7 wherein R$_2$ and R$_3$ together form a double bond between the 17- position carbon atom and the oxygen atom.

9. The method of claim 8 wherein the compound is 3,17-dioxoandrost-4-en-19al.

10. The method of claim 2 wherein R is —CH$_2$OR$_1$.

11. The method of claim 10 wherein R$_2$ and R$_3$ together form a double bond between the 17- position carbon atom and the oxygen atom.

12. The method of claim 11 wherein the compound is 19-hydroxyandrost-4-ene-3,17-dione.

13. A method of contraception in a patient in need thereof which comprises administering to said patient a contraceptive effective amount of an androstene compound of the formula:

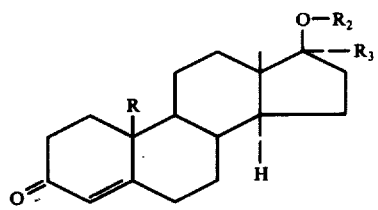

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17- position carbon atom and the oxygen atom; in combination with a non-ovulation inhibiting amount of a progestogen.

14. The method of claim 13 wherein the androstene compound and the progestogen are administered continuously on from day five to day twenty-one of the cycle.

15. The method of claim 13 wherein the androstene compound is administered continuously on from day five to day twenty-one of the cycle and the progestogen is administered on from day sixteen to day twenty-one of the cycle.

16. The method of claim 13 wherein the amount of androstene compound administered is from 0.01 up to 0.3 mg/kg, and the amount of progestogen administered is from 0.005 to 0.5 mg/kg.

17. The method of claim 16 wherein the androstene compound and the progestogen are administered orally.

18. The method of claim 17 wherein the amount of androstene compound administered is from 0.01 to 1.0 mg/kg.

19. The method of claim 13 wherein R is —CHO.

20. The method of claim 19 wherein R$_2$ and R$_3$ together form a double bond between the 17- position carbon atom and the oxygen atom.

21. The method of claim 20 wherein the compound is 3,17-dioxoandrost-4-en-19al.

22. The method of claim 13 wherein R is —CH$_2$OR$_1$.

23. The method of claim 22 wherein R$_2$ and R$_3$ together form a double bond between the 17-position carbon atom and the oxygen atom.

24. The method of claim 23 wherein the compound is 19-hydroxyandrost-4-ene-3,17-dione.

25. An oral contraceptive composition in solid unit dosage form which comprises a contraceptive effective amount of a compound of the formula:

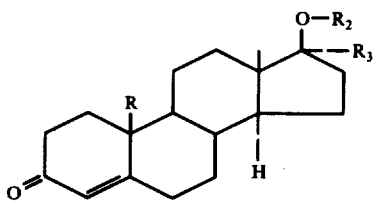

wherein R is —CHO or —CH$_2$OR$_1$; each of R$_1$ and R$_2$ is hydrogen alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$R$_3$ together form a double bond between the 17- position carbon atom and the oxygen atom; a non-ovulation inhibiting amount of a progestogen and a pharmaceutically acceptable carrier.

26. The method of claim 13 wherein the progestogen is 17hydroxy-19-nor-17α-pregn-4-en-20-yn-3-one, 17-hydroxy-19-nor-17α-pregn-4-en-20-yn-3-one acetate, 17-hydroxy-19-nor-17α-pregn-5(10-en-20yn-3-one, 17-hydroxy-19-nor-17α-pregn-4-en-20-yn, 19-nor-17α-pregn-4-en-20-yne-3β,17-diol diacetate, 3-cyclopentyloxy-19-nor-17α-pregna-3,5-diene-20-yn-17ol acetate, 16α(R), 17-](1-phenylethylidene)bis(oxy)]pregna-4-ene-3,20-dione, 17hydroxy-6α-methylpregn-4-ene-3,20-dione acetate, 17α-hydroxy-6-methyl-pregna-4,6-diene-3,20-dione acetate, 17α-hydroxy-6-methyl-16- -methylene-4,6-diene-3,20-dione acetate, 17β-hydroxy-6β-methyl-17-(1-propynyl)androst-4-en-3-one monohydrate, 13-ethyl-17-hydroxy-18,19-dinor-17α-pregn-4-en-20-yn-3-one, and 9β,10α-pregna-4,6-diene 3,20-dione.

27. The method of claim 13 wherein the progestogen is 17-hydroxy-19-nor-17α-pregn-4-en-20-yn-3one acetate, 17-hydroxy- 19-nor-17αpregn-4-en-20-yn, 19-nor-17α-pregn-4-en-20yne-3β,17-diol diacetate or 13-ethyl-17-hydroxy-18,19dinor-17α-pregn-4-en-20-yn-3-one.

28. The composition of claim 25 wherein the progestogen is 17-hydroxy-19-nor-17α-pregn-4-en-20yn-3-one, 17-hydroxy-19-nor-17α-pregn-4-en-20-yn-3-one acetate, 17-hydroxy-19-nor-17α-pregn-5(10)en-20-yn-3-one, 17-hydroxy-19-nor-17α-pregn-4-en-20-yn, 19-nor-17α-pregn-4-en-20-yne-3β,17-diol diacetate, 3-cyclopentyloxy-19-nor-17α-pregna-3,5-diene-20-yn-17-ol acetate, 16α(R),17-](1phenylethylidene)bis(oxy)]-pregn-4-ene-3,20-dione, 17-hydroxy-6α-methylpregn-4-ene-3,20-dione acetate, 17α-hydroxy-6-methylpregna-4,6-diene-3,20-dione acetate, 17α-hydroxy-6-methyl-16-methylene-4,6-diene-3,20-dione acetate, 17β-hydroxy-6α-methyl-17-(1-propynyl)androst-4-en-3-one monohydrate, 13-ethyl-17-hydroxy-18,19-dinor-17α-pregn-4-en-20-yn-3-one, or 9β,10α-pregna-4,6-diene-3,20-dione.

* * * * *